United States Patent [19]

Burnouf-Radosevich et al.

[11] Patent Number: 5,679,776
[45] Date of Patent: Oct. 21, 1997

[54] PROCESS FOR PREPARING A CONCENTRATE OF BLOOD COAGULATION FACTOR VIII-VON WILLEBRAND FACTOR COMPLEX FROM TOTAL PLASMA

[75] Inventors: Miryana Burnouf-Radosevich; Thierry Burnouf, both of Wavrin, France

[73] Assignee: Centre Regional de Transfusion Sanguine de Lille, Lille, France

[21] Appl. No.: 577,368

[22] Filed: Sep. 5, 1990

[30] Foreign Application Priority Data

Sep. 5, 1989 [FR] France ............................. 89 11567

[51] Int. Cl.$^6$ ............................. A61K 38/36; A61K 38/37; C07K 1/30; C07K 1/36
[52] U.S. Cl. ............................. 530/383; 530/415; 530/416; 530/417; 530/420
[58] Field of Search ............................. 530/383, 381, 530/382, 415–417, 420; 514/8

[56] References Cited

U.S. PATENT DOCUMENTS

| | | | |
|---|---|---|---|
| 4,157,431 | 6/1979 | Fields et al. | 525/327.6 |
| 4,361,509 | 11/1982 | Zimmerman et al. | 530/383 |
| 4,386,068 | 5/1983 | Mitra et al. | 530/383 |
| 4,435,318 | 3/1984 | Pabst et al. | 530/381 |
| 4,952,675 | 8/1990 | Mathews et al. | 530/383 |

FOREIGN PATENT DOCUMENTS

| | | |
|---|---|---|
| 0053046 | 11/1981 | European Pat. Off. . |
| 0104356 | 7/1983 | European Pat. Off. . |
| 0176926 | 9/1985 | European Pat. Off. . |
| 0359593 | 2/1989 | European Pat. Off. . |

OTHER PUBLICATIONS

Murray et al. (1988). Harper's Biochemistry. Appleton & Lange, p. 607.

Wang et al. (1988) J. Parenteral Sci. & Tech. vol. 42 (Supp): pp. S1–S26.

*Primary Examiner*—Keith D. Hendricks
*Assistant Examiner*—W. Moore
*Attorney, Agent, or Firm*—Birch, Stewart, Kolasch & Birch, LLP

[57] ABSTRACT

The invention relates to a process for preparing a concentrate of Factor VIII-von Willebrand factor complex having high specific activity from total (non-cryoprecipitated) plasma.

The process comprises pre-purifying by means of a double treatment with barium chloride and with aluminium hydroxide.

The process then comprises purification by chromatography on an anion exchange resin, of the DEAE-Fractogel type.

The process includes a step of viral inactivation by means of a treatment with solvent-detergent.

The process also makes it possible to recover fibrinogen, albumin, immunoglobulins, antithrombin III, fibronectin and prothrombin complex, from the same plasma.

The different concentrates obtained using the process according to the invention are intended, in particular, for therapeutic use.

20 Claims, No Drawings

PROCESS FOR PREPARING A CONCENTRATE OF BLOOD COAGULATION FACTOR VIII-VON WILLEBRAND FACTOR COMPLEX FROM TOTAL PLASMA

The invention relates to a process for preparing a concentrate of Factor VIII-von Willebrand factor complex having high specific activity from total blood plasma.

The treatment of haemophilia A by the injection of Factor VIII is commonly practised and necessitates the use of preparations of high purity, on one hand to reduce the risks of vital contamination and, on the other hand, because the injections have to be repeated frequently, and any residual contaminating material could induce undesirable immune responses dangerous to the patient.

Several methods are already used in industrial centres for the treatment of human plasma to purify Factor VIII. Such methods include precipitation of contaminating proteins using various chemical agents, gel permeation chromatography, immune affinity chromatography, ion exchange chromatography and various combinations of these different methods.

As only a small quantity of Factor VIII is present in the plasma, the yield of the purifying process is the main problem to be solved. Furthermore, Factor VIII is an unstable protein and one that can be activated by other blood factors; however, in activated condition, it loses its therapeutic value; the purifying processes and final dosage will thus have to be adapted to tackle this problem.

The Applicant has already developed a purifying process using ion exchange chromatography which is described in French Patent Application No. 88 07530 and which enables a high purity Factor VIII concentrate to be obtained.

However, in this process, as in those used by other producers, the starting material used is a cryoprecipitated fraction of the plasma. This cryprecipitation stage leads to a loss of 30 to 40% of the Factor VIII, which remains in the supernatent.

It would therefore be an advantage to develop a process of preparation from the non-cryoprecipitated total plasma in order to limit Factor VIII losses. Furthermore, such a process would represent a highly advantageous simplification for inadequately equipped production centres in which it may be difficult to carry out cryoprecipitation.

That is why the Applicant has developed a simple process for purifying Factor VIII from total plasma that makes it possible to obtain a high purity, stable concentrate, and one that gives a very good yield.

The invention thus relates to a process for the preparation of a Factor VIII concentrate from a total plasma. This process includes pre-purifying, to remove the constituents of the prothrombin complex (Factors II, VII, IX, X), and purification by anion exchange chromatography which, through the choice of gel and elution buffer, makes it possible to obtain a Factor VIII-von Willebrand factor complex of high purity.

This process can also be used to obtain, after an additional purification step, purified solutions of the other plasma proteins such as fibrinogen, fibronectin, albumin, immunoglobulins and antithrombin III.

The process was developed using human plasma, but it is equally applicable to a plasma of animal origin.

The process according to the present invention thus makes it possible to use as a starting material a total plasma, that is to say a plasma that is either fresh or frozen in order to preserve it, but not one that is cryoprecipitated. Advantageously, this plasma will have been collected in the presence of an anticoagulant or stabilizing solution. Conventionally, use is made of a citrate-dextrose-phosphate mixture; any specific stabilizer of Factor VIII can advantageously be added thereto or substituted therefor.

A mixture of 0.2 to 2 U/ml of heparin, 1 to 5 mM of EDTA, (ethylenedinitrilo)tetraacetic acid and 1 to 10 mM of $CaCl_2$, with the possible addition of glucose in a concentration of between 5 and 60 g/l, can be advantageously used as a stabilizing solution for the plasma starting material.

The process according to the present invention comprises a first pre-purification step which combines precipitation with barium chloride and adsorption on aluminium hydroxide gel.

Advantageously, the barium chloride treatment is carried out on the plasma, the pH of which is adjusted to 6.5, by adding an 1M barium chloride solution until a final concentration of 0.08M is obtained, with stirring, and the treatment is followed by centrifuging at 5° to 10° C. in order to remove the precipitated proteins, and then by harvesting the supernatant. The precipitated proteins can advantageously be harvested for producing the prothrombin complex or its constituents.

The supernatant is then contacted with 3% aluminium hydroxide gel, at a pH of 6.5, which adsorbs the residual contaminating proteins; this treatment is followed by cooling to 5° to 8° C. in a cryostat, centrifuging at 5° C. and harvesting the supernatant, which is maintained at 5° to 8° C.

This supernatant has to undergo desalting, which can be carried out either by ultrafiltration in the presence of the loading buffer for the following chromatography step to which 0.5 to 2 U/ml of heparin has been added, or by chromatography on SEPHADEX G25 containing a synthetic support comprising a dextran ether in the same buffer.

The process according to the present invention then includes a separation by anion exchange chromatography. The Applicant has already decribed, in French Patent Application No. 88 07530, the advantages that he has revealed of a type of resin having low ion exchange power and large sized pores, the latter permitting the retention of very large sized molecules. This prolonged retention permits the formation of slightly hydrophobic links with the resin and the choice of the ionic strength of the buffer permits selective desorption of the molecules fixed.

Resins of this type are commercially available under the general name of FRACTOGEL. DEAE-FRACTOGEL 650® and T- or D-MAE-FRACTOGEL (Merck) can thus be used. FRACTOGEL is a semirigid gel which is a copolymer of oligoethyleneglycol, glycidylmethacrylate and pentaerythrol-dimethacrylate. These same resins are currently available in a form described by the supplier as that of "tentacular type resins". The structure of their matrix is modified to increase the fixing surface of the positive charges, which can favour an increase in the capacity of the gel.

The loading buffer of the chromatography column is a sodium citrate and sodium chloride based buffer, adjusted to a pH of 7, advantageously containing calcium chloride in a concentration of between 0.5, and 6 mM, lysine in a concentration in the order of 2 to 4 g/l and glycine in a concentration of 8 to 11 g/l. Implementation of the process will include predetermined increases in this sodium chloride concentration.

Implementation of the purifying process according to the invention includes injection of the pre-purified preparation described above on the chromatography column. Under the conditions defined (0.11M NaCl), the column can fix molecules of very large size such as the von Willebrand factor-Factor VIII complex, and allows the fibrinogen, albumin, immunoglobulins, antithrombin III and fibronectin to flow out into the filtrate.

According to a preferred form of embodiment of the invention that aims to achieve optimum Factor VIII recovery efficiency, the ionic strength of the buffer for elution of the chromatography column is increased once only, to 0.27M of sodium chloride. According to another form of embodiment of the invention, this elution step is preceded by pre-washing by increasing the ionic strength to 0.13M of sodium chloride, which removes the fibronectin.

The Factor VIII-von Willebrand factor complex, desorbed and eluted under these conditions, has a specific activity that is at least equal to 5 to 10 U/mg. The overall yield of the process is at least equal to 350 U/litre of initial plasma and can be at least equal to 500 U/litre when the stabilizing mixture described above is added to the initial plasma.

Depending of its subsequent use, this solution of Factor VIII-von Willebrand factor complex can further undergo an additional step of purification and, in particular, concentration by means of another chromatography. Like the previous one, this can be carried out on DEAE- or T/D-MAE-FRACTOGEL or on other resins; other supports, such as dextran sulphate, immobilized amino-hexyl, immobilized heparin, and sulphopropyl resins and affinity or immune affinity resins, can also be used.

This additional chromatography step is carried out in the same basic buffer as the previous one. According to one preferred form of embodiment of the invention which aims to obtain Factor VIII that is as concentrated as possible, this additional chromatography is carried out under the same conditions as the first, that is to say with a single desorption step by increasing the ionic strength of the buffer to 0.27M NaCl. According to another form of embodiment of the invention, a first increase in the ionic strength of the buffer, to 0.13M, is performed to remove the residual contaminating proteins, and a second increase, to 0,27M, is performed to recover the high purity concentrate of Factor VIII-von Willebrand factor complex, which then has a specific activity at least equal to 10 to 20 U/mg.

The other proteins of the first filtrate of the column, such as immunoglobulins, albumin, antithrombin III, fibrinogen and fibronectin, can also be purified and concentrated using conventional chromatographic methods.

The process according to the present invention also includes a vital inactivation treatment according to a known technique. In the event of a chemical agent being used, for example a treatment with a solvent-detergent, it will be advisable to carry out such a treatment prior to any one of the chromatography steps so that the latter ensures the removal of the inactivating agents.

The concentrates of the Factor VIII-von Willebrand factor complex and those of the other plasmatic proteins obtained using the above process are also the object of the present invention.

The said concentrates are formulated in accordance with the standards of the Pharmacopoeia and can be used for therapeutic purposes.

The following examples illustrate two forms of embodiment of the invention without, however, restricting the scope thereof.

EXAMPLE 1

Use is made of 250 ml of fresh plasma or frozen plasma thawed to 22°–25° C., collected in the presence of anticoagulant/stabilizing agent (for example citrate-dextrose-phosphate), and adjusted to a pH of 6.5 with acetic acid.

a) Pre-purification 20 ml of 1M barium chloride at a pH of 6.5 are added thereto by means of a peristaltic pump until a final concentration of 0.08M is obtained. The barium chloride is added at at rate of 4 to 8 ml per minute, and then the mixture is kept stirred, at room temperature, for 15 minutes.

The mixture is then centrifuged at 2 700 r.p.m. for 20 minutes, at 8° C., and then the supernatant is recovered.

The supernatant is then adsorbed on an aluminium hydroxide gel (Alhydrogel Eurobio with 3% $Al(OH)_3$) in a proportion of 2.3 g/l of plasma. The pH is adjusted to 6.5 and the temperature is lowered to 5° C. in a cryostat. The mixture is centrifuged at 5° C. at 2 700 r.p.m. for 20 minutes and the supernatant is recovered and maintained at 5° C.

This treatment makes it possible to eliminate the components of the prothrombin complex (Factors II, VII, IX, X) which can be harvested and purified using known processes.

Particularly satisfactory results can be obtained by combining these two treatments, whereas an Alhydrogel treatment alone will not enable the prothrombin and the other composants of the PPSB to be eliminated completely and a barium chloride treatment on its own will leave behind some Factor X, prothrombin and, above all, Factor VII.

The supernatant thus collected is desalted either by ultra-filtration in the presence of the buffer of the following chromatography step (see below) to which 1 U/ml of heparin has been added, or by chromatography on Sephadex G25, in the same buffer.

A conventional vital inactivation treatment with solvent-detergent is then applied, for 6 hours at 24° C. (This treatment process is described in European Patent Application No. 0 131 740.

b) Purification by chromatography

The pre-purified, dialyzed supernatant undergoes a chromatography purification step. A K26/30 column (Pharmacia-Uppsala Sweden) is used having a diameter of 2.6 cm and a useful height of 30 cm, 10 cm of which are filled with DEAE-Fractogel-TSK 650® resin (Merck).

The composition of the column loading and sample dissolving buffer is as follows: sodium citrate, 10 mM; calcium chloride, 1 mM; glycine, 9 g/l; lysine, 3 g/l. To this buffer is added sodium chloride, adjusted to a final concentration of 0.11M and to a pH of 7.

The sample is injected onto the column at a rate of 100 ml/h.

The column is washed with the loading buffer to remove the non-adsorbed proteins, which include fibrinogen, albumin, immunoglobulins, antithrombine III and fibronectin, as well as the viral inactivating agents.

The Factor VIII-von Willebrand factor complex is then desorbed by increasing the ionic strength of the buffer to 0.27M of sodium chloride.

The Factor VIII solution obtained using this process has a specific activity of 5 to 10 IU/mg and purification efficiency in relation to the plasma injected onto the column is between 60 and 80%.

A ratio close to 1U/1U is always observed for the concentration of the two factors, Factor VIII and von Willebrand factor, the latter being expressed in ristocetin cofactor units.

The purity of this solution of Factor VIII can be further slightly improved by an additional chromatographic separation step which enables the product to be concentrated. Use is made, for example, of a second column of DEAE-FRACTOGEL, under the same loading conditions as before, and pre-washing is carried out with 0.13M of NaCl, which removes the residual contaminating proteins. The ionic strength of the buffer is then increased to 0.27M of sodium chloride to desorb and elute the highly purified and concentrated Factor VIII-von Willebrand factor complex.

The second chromatography concentration step can be replaced by ultrafiltration.

According to the usual form of embodiment of the present invention, the first purification step by chromatography is carried out on a DEAE-FRACTOGEL resin. However, very good results have also been obtained with the new resins marketed by Merck, such as TMAE-FRACTOGEL (TMAE=Tri-Methyl-Amino-Ethyl) or DMAE-FRACTOGEL (DMAE=Di-MAE), which have properties equivalent to those of DEAE-FRACTOGEL. Use can also be made of the new resins of the "tentacular" type developed by the Merck company and presented by W. Müller at the "Conference on Liquid Chromatography", June 1989, in Stockholm.

EXAMPLE 2

Another form of embodiment of the present invention also permits the preparation of concentrates of fibrinogen and fibronectin while, at the same time, providing a Factor VIII-von Willebrand factor concentrate with a lower yield and slightly improved specific activity.

The process is identical with that of example 1, up to the elution of the Factor VIII-von Willebrand factor complex from the first column of DEAE-FRACTOGEL.

The fibrinogen, antithrombin III, albumin and immunoglobulins are not retained by the column and can be recovered in the filtrate.

The Factor VIII-von Willebrand factor complex can be purified and concentrated by a second chromatographic separation step on a column of DEAE-FRACTOGEL, with the loading buffer at an ionic strength of 0.17M of sodium chloride so as not to fix residual contaminating proteins; an increase in the ionic strength to 0.27M of sodium chloride enables the Factor VIII-yon Willebrand factor complex to be desorbed and eluted. A specific activity of 10 to 20 IU/mg is thus obtained.

The fibrinogen and the fibronectin can then be purified and concentrated, using Known chromatographic processes, to give solutions of a quality suitable for therapeutic use and described in French Patent Application No. 88 07530.

The other proteins of the plasma can be purified and concentrated using conventional fractionating processes.

EXAMPLE 3

Purifying efficiency can be improved still further by stabilizing the initial plasma, as from its thawing to 25° C., by adding the following mixture:

Heparin: 1 U/ml

EDTA: 2 mM, or 0.74 g/l

Calcium chloride: 6 mM, or 0.67 g/l.

Glucose at a concentration of between 5 and 60 g/l can further be added to this mixture.

The pH is then lowered to 6.5 by adding acetic acid.

The purification steps are then applied as in Example 1 or 2.

Under these conditions, the overall yield of the purifying process is at least equal to 500 U of FVIII:C/litre of initial plasma.

This corresponds to an overall recovery of 55 to 65% of the activity of Factor VIII for a specific activity of between 10 and 30 units of FVIII:C/mg of protein.

We claim:

1. A process for preparing a stable concentrate of a Factor VIII-von Willebrand factor complex which comprises:
   (a) contacting non-cryoprecipitated total plasma with barium chloride and collecting a first supernatant;
   (b) contacting said first supernatant with aluminum hydroxide gel;
   (c) centrifuging and collecting a second supernatant;
   (d) de-salting said second supernatant;
   (e) contacting said second supernatant with an anion exchange gel, comprising a copolymer of oligoethylene glycol, glycine methacrylate, and pentaerythrol-dimethacrylate; and
   (f) collecting said stable concentrate of Factor VIII-von Willebrand factor complex.

2. Process according to claim 1, wherein said total plasma is a fresh or frozen plasma.

3. Process according to claim 1, wherein said second supernatant is injected onto a chromatography column containing said anion exchange gel which allows fibrinogen, albumin, immunoglobulins, antithrombin III and fibronectin to flow-out into the filtrate.

4. Process according to claim 3, wherein the proteins present in the chromatography filtrate undergo an additional purification and concentration step.

5. The process according to claim 1 or 2, which comprises stabilizing said total plasma in step (a) by adding to said total plasma a stabilizing mixture of 0.2 to 2 U/ml heparin, 1 to 5 mM EDTA, (ethylenedinitrilo)tetraacetic acid and 1 to 10 mM $CaCl_2$.

6. The process according to claim 5, wherein said stabilizing mixture further comprises 5 to 60 g/l of glucose.

7. The process according to claim 1, which comprises adding said barium chloride to said total plasma as a 1M solution at a pH of 6.5, stirring with said total plasma, and centrifuging at 5° to 10° C. and collecting said first supernatant.

8. The process according to claim 1, wherein said aluminum hydroxide gel is a 3% aluminum hydroxide gel having a pH of 6.5; and said centrifuging is conducted at 5° C. to collect said second supernatant.

9. The process according to claim 1, wherein said de-salting treatment is conducted by ultrafiltrating said second supernatant in the presence of a loading buffer and heparin.

10. The process according to claim 1, wherein said de-salting treatment is conducted by contacting said second supernatant with a synthetic support comprising a dextran ether in the presence of a loading buffer and heparin.

11. The process of claims 9 or 10, wherein said loading buffer is a mixture of sodium citrate, calcium chloride, glycine and lysine, and 0.11M sodium chloride, said loading buffer having a pH of 7.

12. The process of claim 11, wherein said glycine is present in an amount of 8 to 11 g/l, and said lysine is present in an amount of 2 to 4 g/l.

13. The process according to claim 1, further comprising conducting a viral inactivation treatment prior to any of steps (b), (d) and (e).

14. The process according to claim 1, wherein said contacting step (e) comprises (i) placing a sample of said second supernatant onto said anion exchange gel, and (ii) washing said anion exchange gel with loading buffer; and said collecting step (f) comprises desorbing and eluting said stable concentrate of Factor VIII-von Willebrand factor complex from said anion exchange gel by increasing the ionic strength of said buffer to 0.27M sodium chloride, and collecting said stable concentrate.

15. The process according to claim 14, wherein said ionic strength is increased to 0.27M sodium chloride in a single step.

16. The process according to claim 14, wherein said ionic strength is increased to 0.27M sodium chloride by (i) increasing said ionic strength to 0.13M sodium chloride, and then (ii) further increasing said ionic strength to 0.27M sodium chloride.

17. The process according to claim 1, wherein said collecting step (f) comprises desorbing and eluting a first stable concentrate of Factor VIII-von Willebrand factor complex from said anion exchange gel, contacting said first stable concentrate with a second ion exchange gel selected from the group consisting of DEAE, a copolymer of oligoethyleneglycol glycine methacrylate, and pentaerythrol-dimethacrylate, linked to diethylaminoethyl groups, or trimethylaminoethyl or dimethylaminoethyl groups, immobilized aminohexyl, immobilized heparin, dextran sulfate, and sulfopropyl resins in the presence of a loading buffer, desorbing and eluting a second stable concentrate of Factor VIII-von Willebrand factor complex, and collecting said second stable concentrate.

18. The process according to claim 17, wherein said loading buffer has an initial ionic strength of 0.11M sodium chloride, and said desorbing and eluting of said second stable concentrate comprises (i) increasing said ionic strength to 0.13M sodium chloride, and then (ii) further increasing said ionic strength to 0.27M sodium chloride.

19. The process according to claim 17, wherein said loading buffer has an initial ionic strength of 0.17M sodium chloride, and said desorbing and eluting of said second stable concentrate comprises increasing said ionic strength to 0.27M sodium chloride in a single step.

20. Factor VIII-von Willebrand factor complex concentrate obtained by the process according to claim 1.

* * * * *